United States Patent [19]

Klug et al.

[11] Patent Number: 5,296,639
[45] Date of Patent: Mar. 22, 1994

[54] ADIPIC ACID PURIFICATION

[75] Inventors: Diana L. Klug, Wilmington, Del.; Johannus H. Van Mil, Ramat Gan, Israel

[73] Assignee: E. I. Du Pont de Nemours and Company, Wilmington, Del.

[21] Appl. No.: 993,276

[22] Filed: Dec. 18, 1992

[51] Int. Cl.$^5$ .............................................. C07C 51/42
[52] U.S. Cl. .................................... 562/593; 562/530; 203/15; 203/48
[58] Field of Search ................ 562/593, 530; 203/15, 203/48

[56] References Cited

U.S. PATENT DOCUMENTS

| | | | |
|---|---|---|---|
| 3,551,300 | 12/1970 | Longley | 203/31 |
| 3,818,081 | 6/1974 | Adamek | 260/537 P |
| 4,254,283 | 3/1981 | Mock | 562/593 X |
| 4,874,700 | 10/1989 | Seipenbusch | 562/593 X |
| 5,034,105 | 7/1991 | Berglund et al. | 562/593 X |
| 5,104,492 | 4/1992 | King et al. | 562/593 X |

FOREIGN PATENT DOCUMENTS

| | | |
|---|---|---|
| 1938103 | 3/1991 | Fed. Rep. of Germany . |
| 54-115314 | 9/1979 | Japan . |
| 1216844 | 3/1991 | United Kingdom . |

OTHER PUBLICATIONS

Addadi et al., Angew. Chem. Int. Ed. Engl., vol. 24, pp. 466–485 (1985).
Shimon et al., Nouveau J. de Chemie, vol. 10, No. 12, pp. 723–737 (1986).
Addadi et al., Top. Stereochem., 16, 1 (1986).

Primary Examiner—Arthur C. Prescott

[57] ABSTRACT

A process for purification of adipic acid during crystallization by modifying the crystal morphology to decrease incorporation of impurities through the introduction of an effective amount of an additive to the crystallizing solution.

7 Claims, 11 Drawing Sheets

FIG.3a 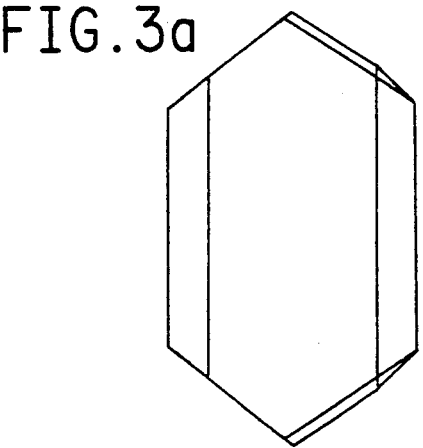 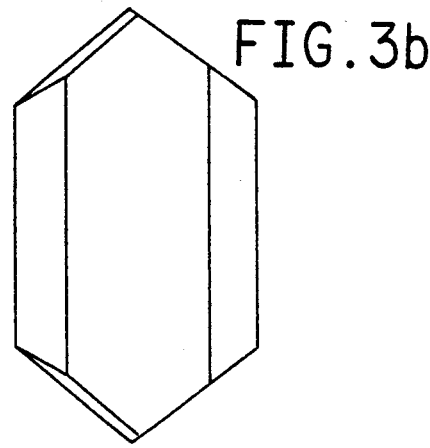 FIG.3b
FIG.3c  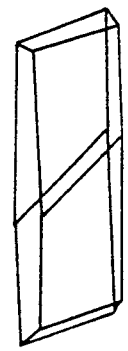 FIG.3d
FIG.3e   FIG.3f

ADIPIC ACID PURIFICATION

FIELD OF THE INVENTION

The present invention relates to a process for purification of adipic acid during crystallization through control of crystal morphology. The use of surfactants to control crystal habit decreases the level of impurities.

BACKGROUND OF THE INVENTION

Systematic modification of the morphology of crystals can be achieved by tailoring additives which bind at a preselected crystal face, and thus inhibit growth in a predictable manner. Morphological changes associated with the growth of organic crystals in the presence of additives results from the high degree of specificity in the interaction of the foreign material with the different structured surfaces of the crystalline matrix. In general, when growth is inhibited in a direction perpendicular to a given crystal face, the area of this face increases relative to those of the other faces of the crystal. The additive is adsorbed only at those faces in which the part of the adsorbate that differs from that of the substrate points away from the crystal interior. Once adsorbed, the additive inhibits the regular deposition of oncoming layers of crystal substrate molecules, slowing down the growth perpendicular to that face and leading to a relative increase in its surface area.

Addadi et al. in Angew. Chem. Int. Ed. Engl., Vol. 24, pp. 466-485 (1985) disclose that when crystals of organic compounds are grown in the presence of growth inhibitors, there is a change in crystal morphology, and a stereochemical correlation exists between the modified morphology, crystal structure and the molecular structure of the inhibitor. This correlation has been exploited to resolve conglomerates, to engineer crystals with desired morphologies, to assign the absolute configuration of chiral molecules and crystals, and to design models for generation of optical activity. The dissolution of organic crystals in the presence of inhibitors is also described.

Shimon et al. in Nouveau Journal de Chemie, Vol. 10, No. 12, pp.723-737 (1986) disclose a general method for the controlled stereoselective etching of preselected faces of organic crystals. The method is based on a correlation between the molecular structure of the etchant and the organic crystals, and has been applied for sorting of enantiomorphs, assignment of configuration of chiral molecules, and assignment of the structure of polar crystals.

Japanese Patent Application 54115314 published Sep. 7, 1979 discloses recovery of adipic acid from a mixture of glutaric acid, succinic acid, and adipic acid by adding an inorganic potassium salt to the solution, separating the adipic acid by crystallization, and then purifying the adipic acid.

U.S. Pat. No. 3,818,081 issued Jun. 18, 1974 discloses separation of adipic acid from mixtures with glutaric and succinic acids by treatment with anhydrous ammonia.

The formation or presence of byproducts and impurities is an inherent and recurring problem in organic synthesis as well as manufacturing operations. Adipic acid synthesis results in a large number of impurities which are incorporated during crystallization, some of which are present in larger quantities and pose a quality problem. The most common ones are succinic, glutaric, and caproic acid, but others like fumaric, maleic, hydroxy caproic acid, and cyano valeric acid have been detected. The removal of such impurities by conventional means is often hindered by the similarity in solubility, chemical properties, and crystal structure between impurity and substrate.

The present invention provides a method of purification of adipic acid during crystallization through control of the accessibility of molecules to crystal growth sites thereby modifying crystal morphology. The present invention also provides a method of purification of adipic acid during crystallization by addition of caproic acid, or by addition of a surfactant which remains substantially unadsorbed.

SUMMARY OF THE INVENTION

The present invention comprises a process for purification of adipic acid during crystallization comprising modifying the crystal morphology to decrease incorporation of impurities by introduction of an additive to the crystallizing solution. Introduction of an effective amount of an additive to the crystallizing solution which binds at a particular crystal face inhibits the growth of this face relative to other unaffected crystal faces. Thus the additive reduces impurity adsorption by decreasing the surface area of the faces to which the impurities bind. Suitable additives include caproic acid and selected surfactants. The surfactants provide the additional advantage of remaining substantially unincorporated by the adipic acid crystals, and of improving the filtration and flow properties of the resulting crystals. The present invention further comprises a process for improving the flow properties of a crystallizing solution of adipic acid comprising introducing an effective amount of a surfactant to said solution.

BRIEF DESCRIPTION OF THE FIGURES

FIGS. 3a through 3f depicts crystals of adipic acid with 3% succinic acid, which are plates with {100} faces as the main faces lined by {001}, {102} and {011} faces.

DETAILED DESCRIPTION OF THE INVENTION

Figure 1A:
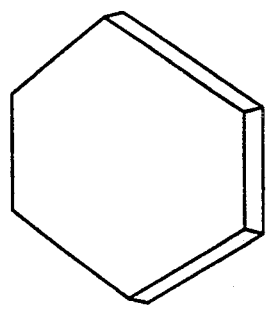
FIGS. 1a through 1f depicts crystals of pure adipic acid, which are plates with {100} faces as the main faces and are lined by the {001} and {011} faces.
Figure 1B:
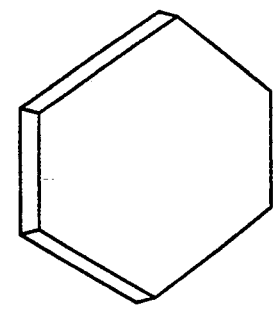
Figure 1C:
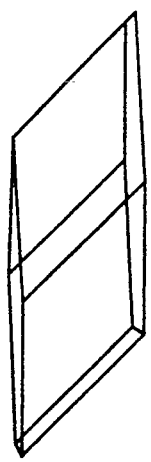
Figure 1D:
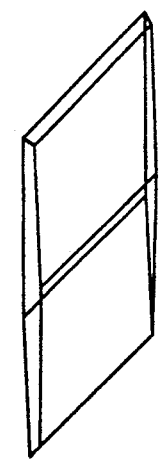
Figure 1E:
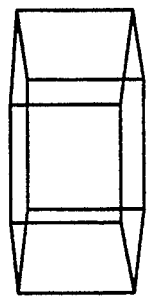
Figure 1F:
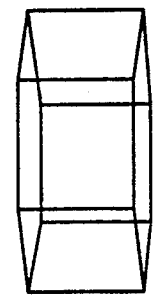
Figure 2A:
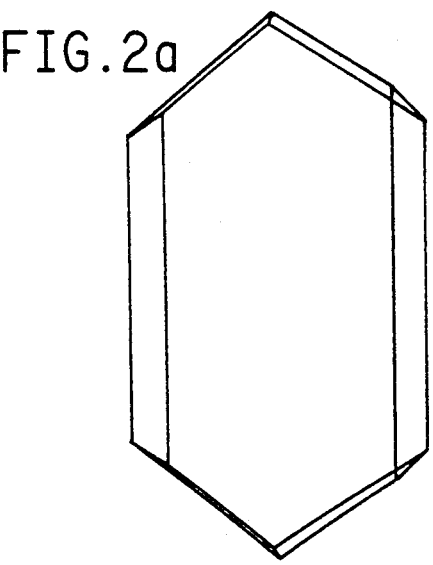
FIGS. 2a through 2f depicts crystals of adipic acid with 3% glutaric acid, which are plates with {100} faces as the main faces lined by {001} and {011} faces or faces similar to these such as {102} or {144}.
Figure 2B:
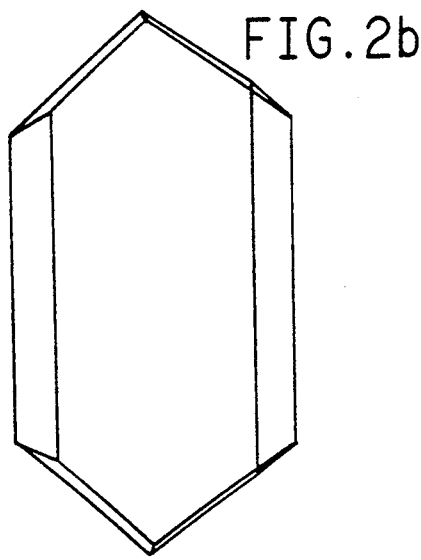
Figure 2C:
Figure 2D:
Figure 2E:
Figure 2F:
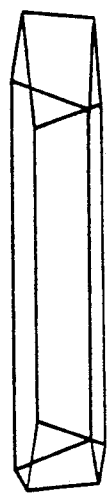
Figure 4A:
FIGS. 4a through 4f depict crystals of adipic acid with 3% caproic acid, which are very thin plates with {001} faces as the main faces lined by {201} and {110} faces.
Figure 4B:
Figure 4C:
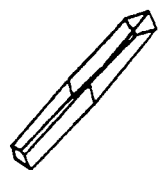
Figure 4D:
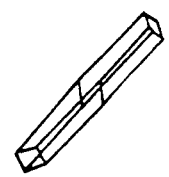
Figure 4E:
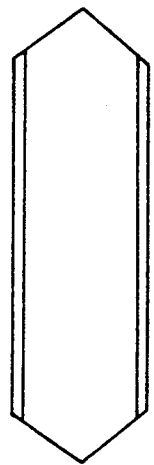
Figure 4F:
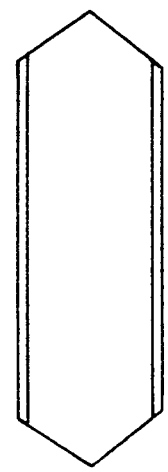
Figure 5A:
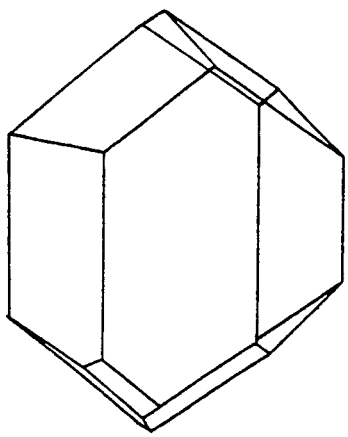
FIGS. 5a through 5f depict crystals of adipic acid with 3% maleic acid, which are thick plates with {100} faces as the main faces and a large number of smaller faces.
Figure 5B:
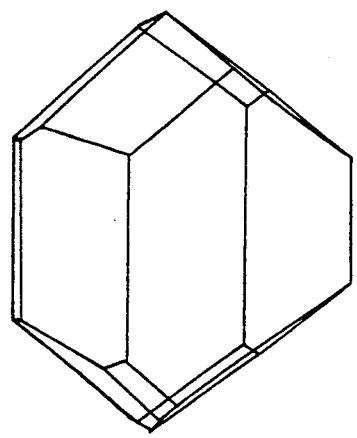
Figure 5C:
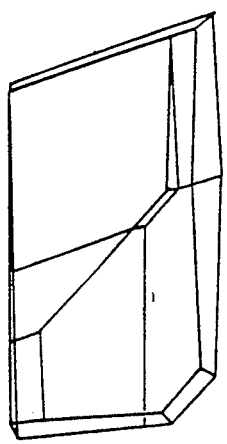
Figure 5D:
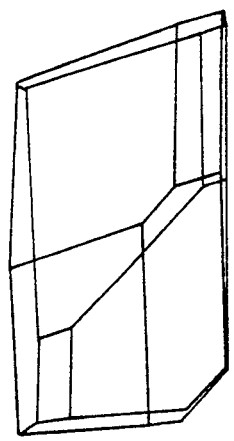
Figure 5E:
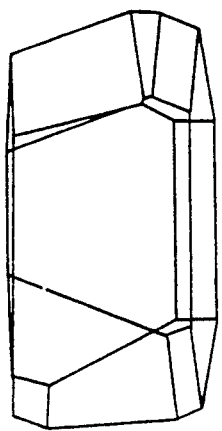
Figure 5F:
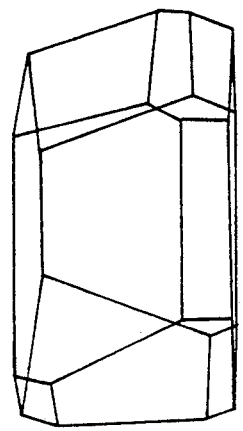
Figure 6A:
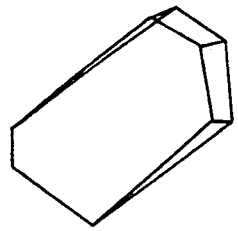
FIGS. 6a through 6f depict crystals of adipic acid with 3% fumaric acid, which are plate-like with (-1-11) and (21-1) faces as the main faces, and relatively insignificant {001} faces.
Figure 6B:
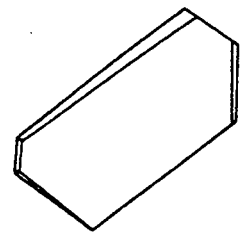
Figure 6C:
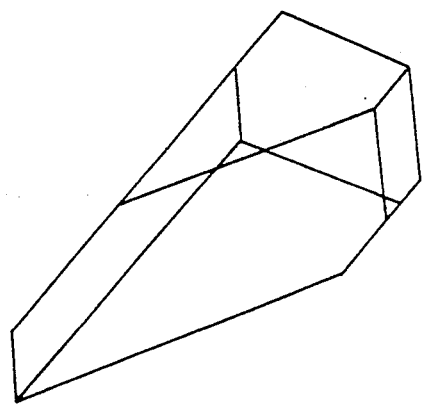
Figure 6D:
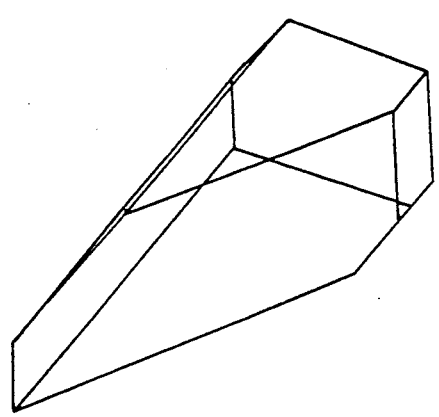
Figure 6E:
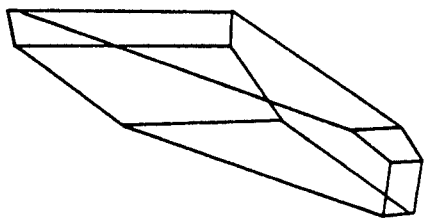
Figure 6F:
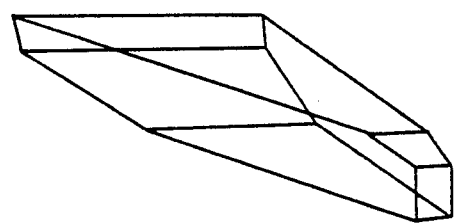

Adsorption and incorporation of impurities during adipic acid crystallization takes place at specific surfaces of the crystal where appropriate lattice sites are exposed. Such adsorption/incorporation results in changes in the overall habit of the crystal. Thus, habit changes in the acid crystal as a result of an impurity can be directly correlated to specific lattice sites. Impurity incorporation can be limited or prevented by the method of the present invention wherein the morphology of the acid crystal is manipulated to decrease or prevent adsorption and incorporation.

Crystals of pure adipic acid exhibit a plate morphology with {100} faces as the main faces. The plates are lined by the {001} and {011} faces. See FIG. 1. The presence of either succinic acid or glutaric acid during crystallization of adipic acid makes the plate-like character more pronounced. The {100} faces increase in size to about 60% of the crystal surface from less than 50% in the pure crystal., and overall the plates become increasingly thinner. This is illustrated in FIGS. 2 and 3. Table I in Example 1 hereinafter provides data showing the increase in the relative surface area of the {100} face relative to the total surface area of the crystal with increasing concentrations of succinic or glutaric acid present during crystallization.

The presence of caproic acid during adipic acid crystallization changes the morphology of the crystal to yield a thin plate with the {001} faces as the main faces. This is illustrated in FIG. 4. While in pure adipic acid crystals these faces are rather insignificant, the presence of 1% of caproic acid during crystallization elevates them to about 75% of the total surface area, and 3% of caproic acid to about 90%. Quantities as small as 0.01% caproic acid yield crystals with the {001} faces as the most significant.

The presence of maleic acid during adipic acid crystallization does not have a significant effect on crystal morphology. Crystal are thick plates with the {100} faces as the main faces as shown in FIG. 5. A large number of smaller faces indicates that adsorption of maleic acid is not very selective or effective.

The presence of fumaric acid during adipic acid crystallization changes the crystal morphology to yield plate-like crystals with the (-1-11) and (21-1) faces as the main faces as shown in FIG. 6.

Thus, of the commonly occurring impurities in adipic acid, succinic or glutaric acid increase the size of the {100} faces, while caproic acid increases the size of the {001} faces during crystallization. These two effects on the crystal morphology are directly opposed.

The effect of the caproic acid on the {001} faces is stronger than that of succinic or glutaric acid on the {100} faces. A concentration of 1% of succinic or glutaric acid in the adipic acid crystallizing solution results in an approximate increase of about 10% in the surface area of the {100} faces, while a 1% concentration of caproic acid in the crystallizing solution results in an approximate increase of about 800% in the surface area of the {001} faces. This, combined with the diametrically opposed directions of the effect of the impurities has important consequences for their combined effect. Caproic acid will always be a much more effective modifier of the habit of the adipic acid crystal, unless very lopsided ratios are used.

Since the amount of impurity incorporated should be directly proportional to the surface area of the face it affects, this indicates that when caproic acid is present simultaneously with either succinic or glutaric acid in the crystallizing solution of adipic acid, the incorporation of each is strongly influenced by the effect on morphology of the other. In particular, since caproic acid is incorporated through the {001} faces and results in a crystal morphology where these faces are the main ones, leaving the {100} faces insignificant in size, succinic acid and glutaric acid, which adsorb on these {100} faces are partially prevented from being incorporated into the crystal. Therefore significant reductions in the level of succinic acid or glutaric acid in adipic acid crystals can be achieved in the presence of caproic acid. Reductions of up to about 70% are possible.

Figure 7:
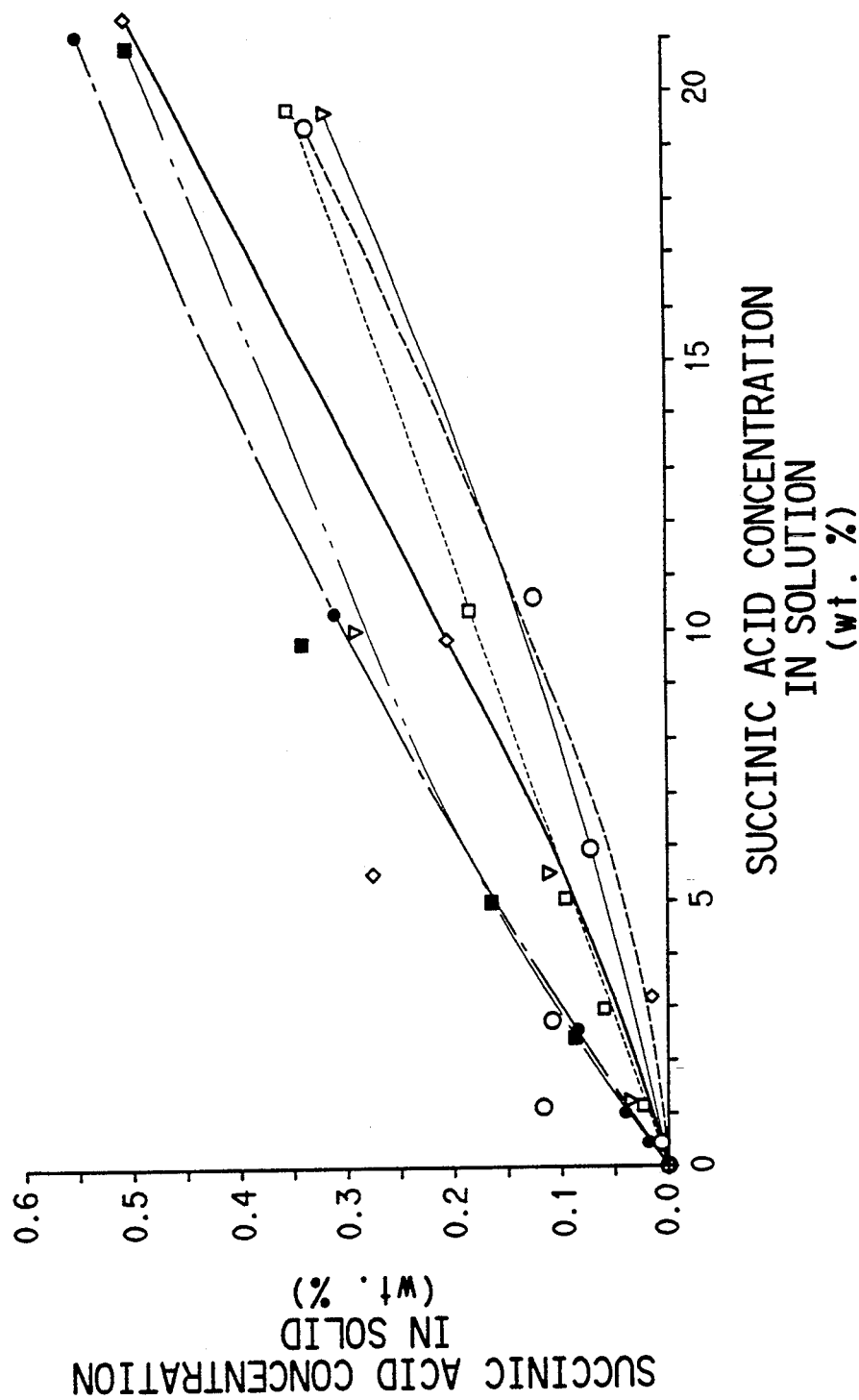
FIG. 7 depicts a graph of succinic acid concentration in solution versus succinic acid concentration in the solid during adipic acid crystallization, and shows the effect of the presence of caproic acid in decreasing succinic acid incorporation. Controls are denoted by black squares and circles. White circles, squares, triangles and diamonds denote 3%, 1%, 0.5% and 0.1% by weight of caproic acid respectively.

The effect on succinic acid incorporation of the presence of caproic acid is shown in FIG. 7. A significant reduction in succinic acid levels occurs over the full concentration range of from 0.5% to 20% by weight present in the crystallizing solution. The amount of caproic acid present does not dramatically alter the effect, except when the ratio of succinic to caproic acid is very large (greater than 100). Typically from about 0.1 to about 3.0% by weight caproic acid is added. The amount of caproic acid adsorbed by the adipic acid crystals during formation is largely identical to the amount adsorbed when no succinic acid is present. Similar results can be achieved with caproic acid in the presence of glutaric acid.

Morphology also has a significant effect on physical properties like hydrophobicity of the crystal. A recurrent problem in adipic acid crystallization is the tendency of crystals to float. Floating crystals will grow along one particular axis or another depending upon what faces are pointing toward the solution and what faces are pointing away from the solution. Crystal orientation is thus affected by the hydrophobic character of the atoms or side chains present.

The addition of small amounts of surfactant to the adipic acid crystallizing solution prevents the float phenomenon and gives rise to crystals free flowing in the solution. Thus the flow properties of adipic acid crystal slurries are improved. The surfactant also extensively affects the crystal morphology. The crystal is transformed into a flat needle having {001} faces as the dominant faces. This is illustrated in FIG. 9. The {001} faces constitute about 65% of the crystal surface area. This is similar to the effect of caproic acid on the crystal morphology. Thus the presence of a surfactant in the adipic acid crystallizing solution decreases incorporation of succinic or glutaric acid into the adipic acid crystals.

Figure 8:
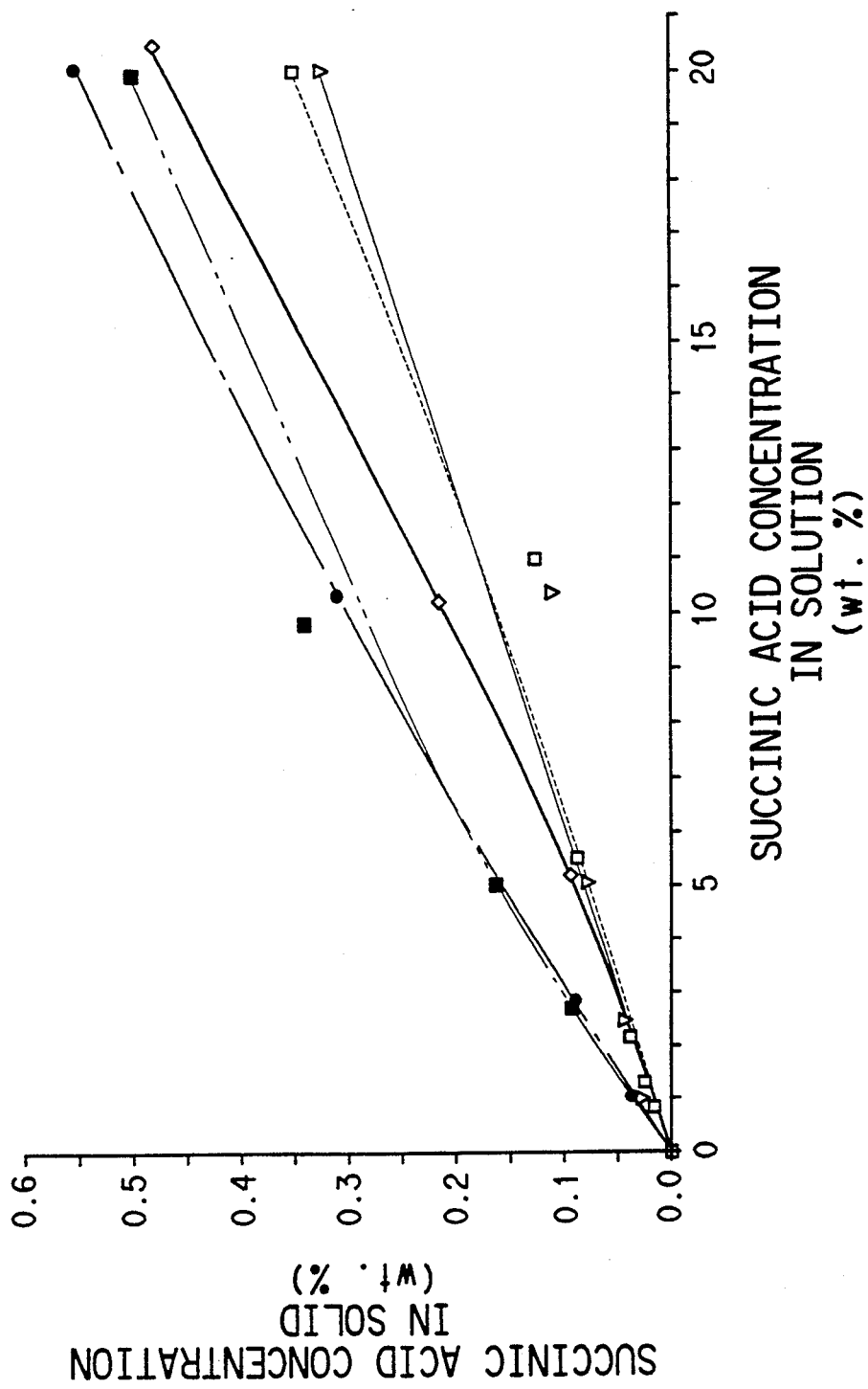
FIG. 8 depicts a graph of succinic acid concentration in solution versus succinic acid concentration in the solid during adipic acid crystallization, and shows the effect of the presence of sodium dodecyl sulfate in decreasing succinic acid incorporation. Controls are denoted by black squares and circles. White squares, triangles, and diamonds denote 1%, 0.5%, and 0.1% by weight of sodium dodecyl sulfate.
Figure 9A:
FIGS. 9a through 9f depict crystals of adipic acid crystallized in the presence of a surfactant, which are flat needles with {001} faces as dominant faces.
Figure 9B:
Figure 9C:
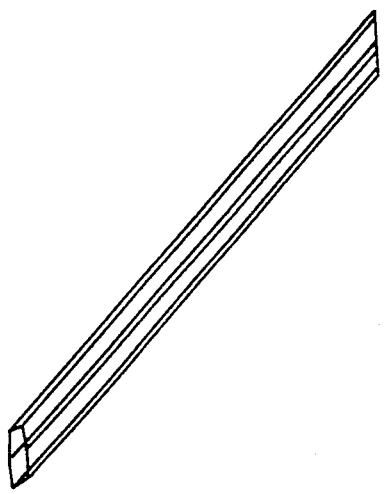
Figure 9D:
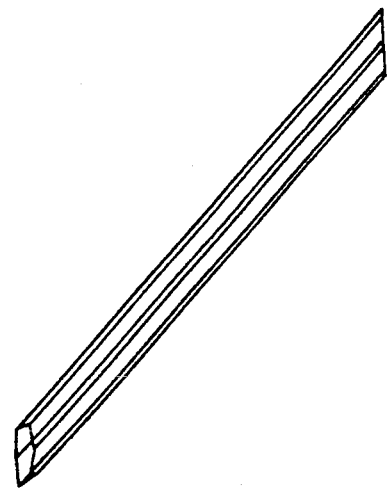
Figure 9E:
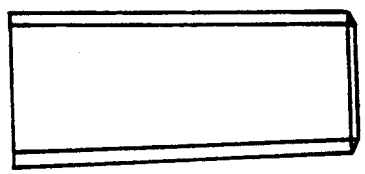
Figure 9F:
Figure 10:
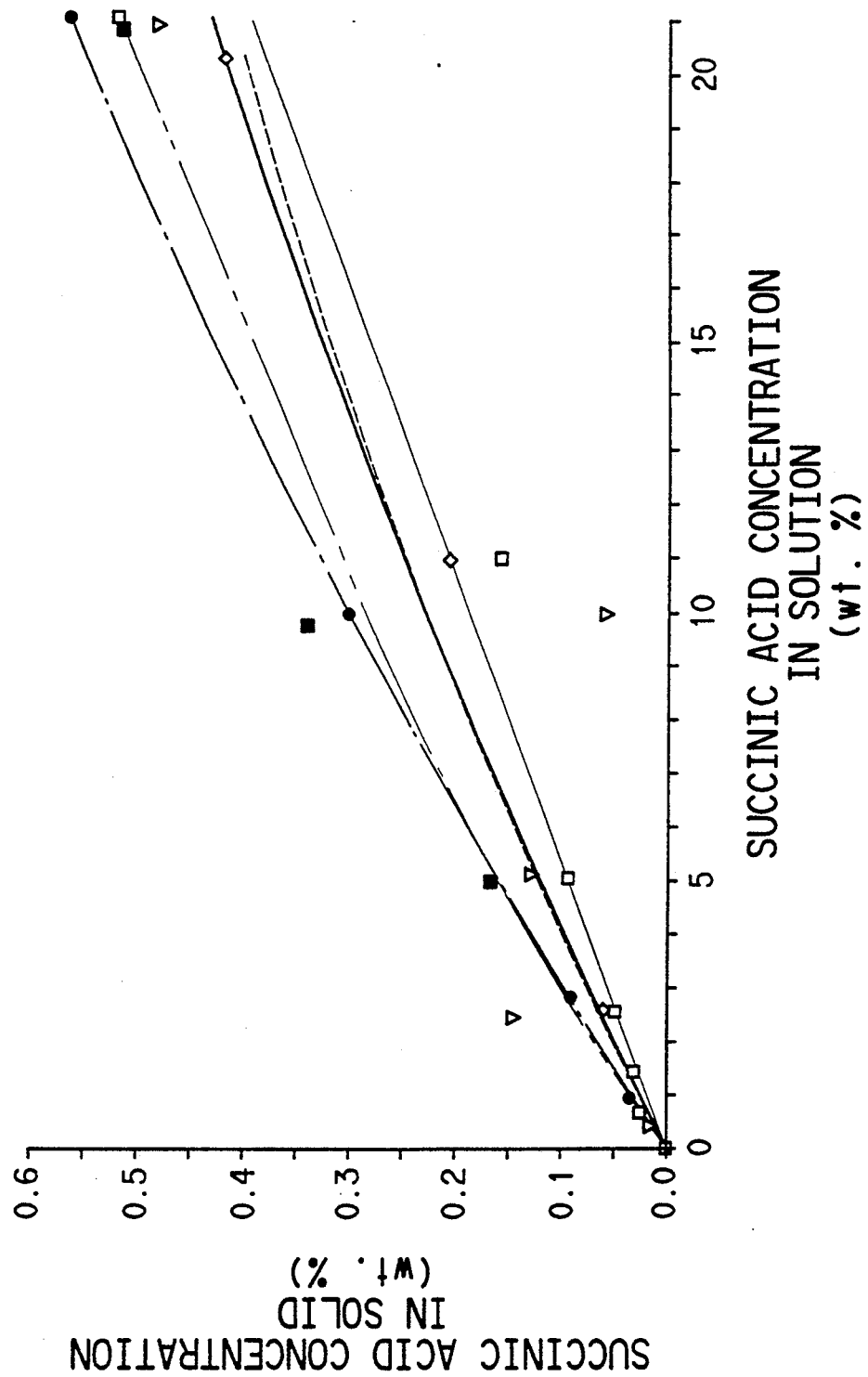
FIG. 10 depicts a graph of succinic acid concentration in solution versus succinic acid concentration in the solid during adipic acid crystallization, and shows the effect of the presence of sodium dodecyl sulfonate in decreasing succinic acid incorporation. Controls are denoted by black squares and circles. White squares, triangles, and diamonds denote 1%, 0.5%, and 0.1% by weight of sodium dodecyl sulfonate.
Figure 11:
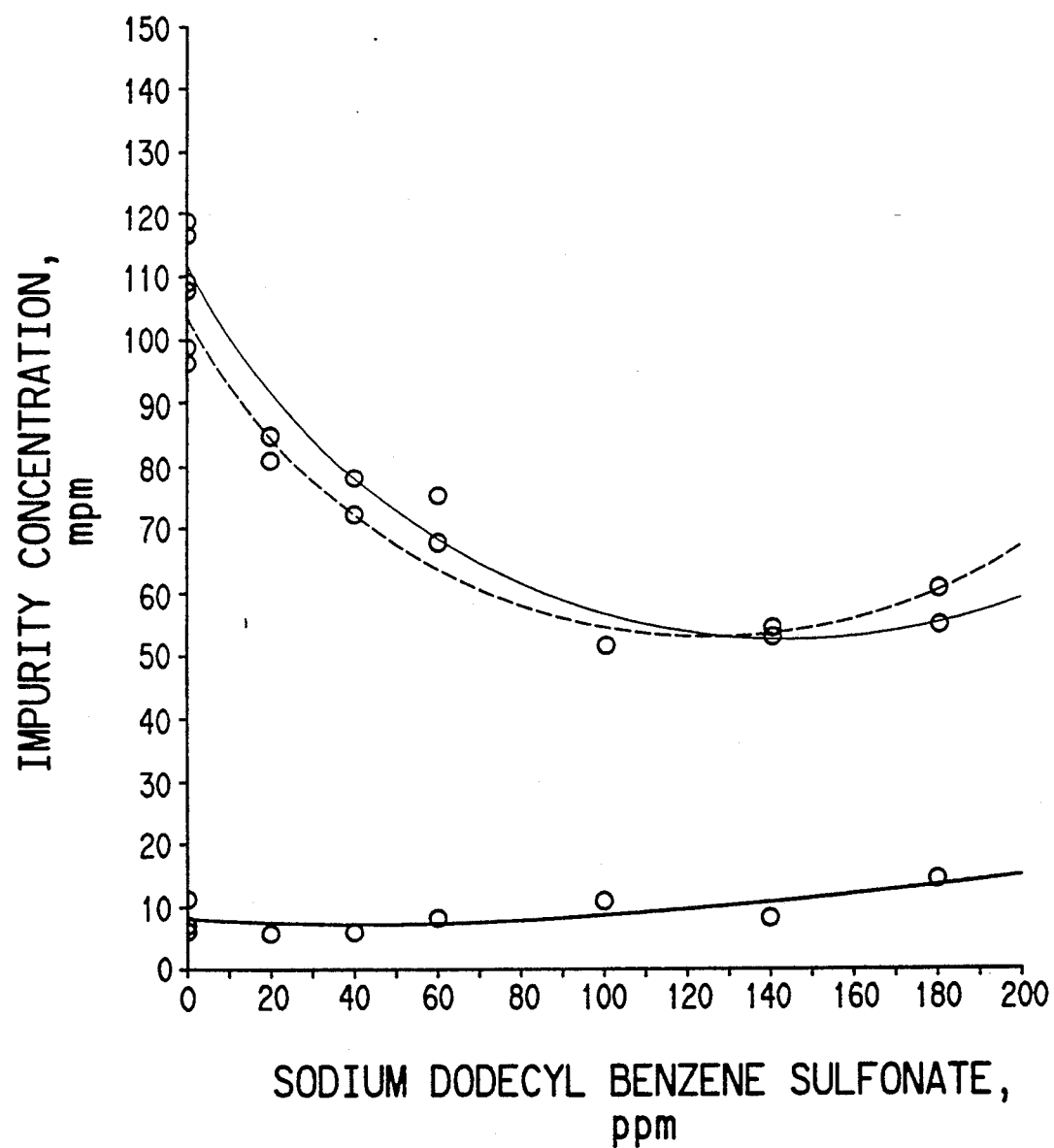
FIG. 11 depicts a graph of impurity concentration versus additive concentration during adipic acid crystallization from a manufacturing solution, and shows the effect of the presence of sodium dodecyl benzene sulfonate. Line A denotes succinic acid, line B denotes glutaric acid, and line C denotes caproic acid. The impurity concentration is in moles per million (mpm). The surfactant concentration is in parts per million ($\mu$g/g).

Surfactants suitable for use herein comprise water soluble surfactants, preferably anionic surfactants. Examples include sodium dodecyl sulfate, sodium dodecyl benzene sulfonate, or sodium lauryl sulfate. The amount of surfactant employed is preferably minimized. Where it is required to remove relatively small amounts of impurities from adipic acid, use of about 150 ppm of the surfactant will produce satisfactory results. When much more of the impurities are present, larger amounts of surfactant are required. Typically from about 0.1% to about 1.0% by weight is effective. The effect of the presence of sodium dodecyl sulfate on succinic acid incorporation during adipic acid crystallization is illustrated in FIG. 8. A similar effect for sodium dodecyl sulfonate is illustrated in FIG. 10.

One advantage of use of a surfactant over use of caproic acid to reduce the levels of impurities during crystallization of adipic acid is that the surfactant remains substantially unincorporated. Typically levels of surfactant found in the adipic acid crystals is less than 0.1%.

The processes of the present invention are useful in economical commercial production of adipic acid. The sequence of removal of impurities can be arranged to take advantage of the effect of the presence of caproic acid has in decreasing the level of succinic and glutaric acids. When residual levels of surfactant are acceptable in the adipic acid product, their use provides an efficient means to control crystal flow problems due to floating crystals while simultaneously decreasing the level of impurities in the crystalline product.

The process of this invention is not dependent upon the presence or absence of any of the normal by-products of adipic acid synthesis, i.e., the process of this invention works over a broad range of impurity levels ranging from part per millions of impurities up to 20% succinic and 20% glutaric acids, for example.

The process of this invention will work in the range of temperature from ambient to about 90° C. The mode of washing or filtering of the crystals does not affect the process of the present invention.

The process of this invention is not dependent upon any particular mode of crystallization, nor does the method of cooling have an effect; vacuum cooling or jacket cooling are equally applicable. Both batch processing and large scale continuous processing are equally applicable.

The method of purification described here, the use of stereo-selective additives to modify the preparation of impurity-containing faces, can be generally applied to other systems or processes. In such cases, an additive must be chosen which selectively adsorbs on faces not affected by impurities. In this manner, the amount of impurity incorporated in the product to be crystallized could be reduced.

The following examples illustrate the present invention but are not intended to limit it in any way.

EXAMPLE 1

Crystals of adipic acid were grown from water, by slow cooling of about 0.5 degrees per day from 65° C. to ambient room temperature. Crystals were grown both from the pure material as well as in the presence of the following impurities: succinic, glutaric, caproic, maleic, and fumaric acids. The detailed morphologies of these crystals were measured, including face indexing using the methods of L. Addadi et al., Angew. Chem. Int. Ed. Engl. 24, 466-485 (1985) which is herein incorporated by reference, and are summarized in Table I.

TABLE I

Pure Adipic Acid:
Crystals were plates with {100} faces as the main faces. The plates were lined by {001} and {011} faces.
Adipic Acid with Glutaric Acid:
Crystals were plates with {100} faces as the main faces. Plates were lined by {001} or {011} faces, or faces similar to these such as {102} or {144}. Crystals became thinner with increasing concentration of glutaric acid.
Adipic Acid with Succinic Acid:
Crystals were plates with {100} faces as the main faces. Plates were lined by {001}, {102}, and {011} faces. Crystals became thinner with increasing concentration of succinic acid.
Adipic Acid with Caproic Acid:
Crystals were thin plates with {001} faces as the main faces. Plates were lined by {201} and {110} faces. Crystals became less well formed with rounded edges with increasing concentration of caproic acid.
Adipic Acid with Maleic Acid:
Crystals were thick plates with {100} faces as the main faces. A large number of smaller faces were present.
Adipic Acid with Fumaric Acid:
Crystals were plate-like with (−1-11) and (21-1) as the main faces. The {001} faces were relatively insignificant, and no {100} faces were present.

Increasing amounts of impurity resulted in a more pronounced morphological effect. Both glutaric acid as well as succinic acid yielded increasingly thinner plates, or relatively larger {100} faces as the concentration of these acids increased in the crystallizing solution. The data obtained are listed in Table II.

TABLE II

| Impurity | Percentage | {100} Surface Relative to Total Surface, % |
|---|---|---|
| None | — | 48.6 |
| Glutaric | 0.5 | 57.1 |
| Glutaric | 1.0 | 57.9 |
| Glutaric | 3.0 | 72.5 |
| Succinic | 0.5 | 57.0 |
| Succinic | 1.0 | 59.5 |
| Succinic | 3.0 | 63.7 |

Caproic acid showed a similar trend for {001} faces. While in pure adipic acid crystals these faces were rather insignificant, 1% of caproic acid present in the crystallization solution elevated them to 75.9% of the total surface, and 3% caproic acid present in the crystallizing solution elevated them to 86.6%. A concentration of caproic acid as low as 0.01% in the crystallizing solution yielded crystals with the {001} faces as the most significant.

EXAMPLE 2

A quantity (2000 ml) of impurity-laden adipic acid solution was charged to a stirred, glass crystallizer. The composition of the solution was 47% adipic, 42% nitric, 2073 ppm succinic, and 42 ppm caproic. Glutaric was not measured, but estimated to be approximately 3000 ppm. Other normal impurities from a manufacturing process were present, but were not measured. To the mixture was added the surfactant, sodium dodecylbenzene sulfonate, to give a concentration on a per weight basis of 130 ppm. The resulting mixture was heated to 85° C. and held there for approximately ½ hour until all the adipic acid crystals had dissolved. The mixture was subsequently cooled, while stirring, until 60° C. was reached, where upon, a sample of the slurry was removed from the crystallizer. The slurry was filtered to remove adipic acid crystals, and dried. The dried adipic acid crystals, purified as described above, were found to contain approximately 54 ppm of glutaric, and 73 ppm of succinic acids. Purification in the absence of the surfactant, but using the same exact procedure, yielded crystals containing 136 ppm of glutaric, and 161 ppm of succinic acids.

EXAMPLE 3

The process of Example 1 was repeated, except that the crystals, after filtration, were rinsed with ice water, and then dried. The crystals so obtained were found to have approximately 11 ppm of succinic and 7 ppm of glutaric, whereas the crystals produced by the same process in the absence of the additive, had concentrations of 21 ppm succinic and 16 ppm of glutaric.

EXAMPLE 4

A solution of adipic acid containing quantities of impurities was pumped continuously to a stirred tank reactor where the contents were cooled, and a stream of slurry continuously discharged. To the inlet stream of adipic acid was added the surfactant sodium dodecylbenzene sulfonate, such that the concentration in the crystallizer was approximately 100 ppm. The resulting slurry was filtered, the filter cake washed, and the recovered solids dried. The resulting concentration of cyanovaleric acid was 1.7 ppm whereas crystals produced by the same process without the surfactant had 23 ppm of cyanovaleric acid. The crystals produced in the presence of the surfactant were also more equiaxed, and had superior flowability characteristics than the crystals produced in the absence of the surfactant.

What is claimed is:

1. A process for purification of adipic acid during crystallization comprising modifying the crystal morphology to decrease incorporation of impurities by introduction of an additive to the crystallizing solution.

2. The process of claim 1 wherein the morphology of the adipic acid crystal is modified to create a flat needle crystal having {001} faces as the dominant faces.

3. The process of claim 1 wherein the additive is caproic acid.

4. The process of claim 1 wherein the additive comprises a surfactant.

5. The process of claim 4 wherein the surfactant is sodium dodecyl sulfate, sodium dodecyl sulfonate, or sodium dodecyl benzene sulfonate.

6. The process of claim 1 wherein the additive is present in the crystallizing solution in an amount of from about 0.1% to about 3.0% by weight.

7. A process for improving the flow properties of a crystallizing solution of adipic acid comprising introducing an effective amount of a surfactant to said solution.

* * * * *